United States Patent [19]

Nakashima

[11] Patent Number: Plant 6,032

[45] Date of Patent: Oct. 6, 1987

[54] ROSE PLANT NAMED DE VINK

[75] Inventor: Tosh Nakashima, San Leandro, Calif.

[73] Assignee: DeVor Nurseries, Inc., Pleasanton, Calif.

[21] Appl. No.: 773,291

[22] Filed: Sep. 6, 1985

[51] Int. Cl.[4] ..... A01H 5/00
[52] U.S. Cl. ..... Plt./22
[58] Field of Search ..... Plt./22, 26-27

*Primary Examiner*—Robert E. Bagwill
*Attorney, Agent, or Firm*—Chas. W. Rummler; John B. Lungmus

[57] ABSTRACT

A new and distinct variety of greenhouse floribunda rose plant which originated as a sport of the variety "Mary DeVor" (U.S. Plant Pat. No. 2,838) and is particularly distinguished by the fuchsia purple color of its flowers which sharply contrasts with the cardinal red color of the blooms of the parent plant. This new rose plant variety retains the parent plant advantages of profuse year around flowering, the relatively small size of the flowers which are supported by strong flower stems, and the long lasting character of the blooms both on the plant and as cut flowers, all of which provides an excellent variety for cut flower production.

3 Drawing Figures

BACKGROUND OF THE INVENTION

This new rose plant sport was discovered by me in 1982 among a field of the variety "Mary DeVor" growing in my greenhouses at San Leandro, Calif., and the very unusual color of its flower prompted me to reproduce this sport by budding and this method of reproduction has been carried through several successive generations, both at San Leandro and at Pleasanton, Calif., which have demonstrated that this new variety has retained most of the advantageous characteristics of the parent "Mary DeVor" and that its distinctive characteristics, particularly color, remain true from generation to generation and appear to be firmly fixed.

DESCRIPTION OF THE DRAWING

My new rose plant is illustrated by the accompanying photographic drawings, of which sheet one shows a full face view of the new flower together with some of the foliage; and sheet two shows in the upper view a series of buds in progressive stages of opening, and in the lower view front and reverse side views of typical leaves, a bud just about to begin opening, the base of a fully opened flower after the petals have been removed, and specimens of old and young wood; the color rendition in all views being as nearly true as it is reasonably possible to obtain by conventional photographic procedures.

DESCRIPTION OF THE NEW VARIETY

The following is a detailed description of my new rose plant as observed at Pleasanton, Calif., with color designations according to The R.H.S. Colour Chart published by The Royal Horticultural Society of London, England.

THE PLANT

Origin: Sport.
Parentage: "Mary DeVor", U.S. Plant Pat. No. 2,838.
Classification:
- *Botanic.*—Hybrid Floribunda.
- *Commercial.*—Greenhouse Rose.

Form: Tall, upright bush.
Height: About 156 to 191 cm.

Main stem or cane length: 44 to 62 cm. from the hook.
Growth rate: Approximately 45 days.
Color stems and branches: Green, RHS 139C.
Branching character: The plant is well branched.
Growth character: Vigorous and upright.
Strength: Canes are slender but sturdy.
Foliage:
- *Quantity.*—Abundant.
- *Color.*—Green, RHS 139A.
- *Number of leaves.*—About 7 to 10 from the hook.
- *Leaf size.*—About 5.7 cm. long and about 3.4 cm. wide.
- *Rachis.*—About 5.4 cm. long.

Leaflets:
- *Number.*—3 to 5.
- *Size.*—About 4.1 cm. long and 1.7 cm. wide on leaf have three leaflets and about 3.5 cm. long and 3.0 cm. wide on leaf having five leaflets.
- *Shape.*—Oval with cuspidate apex and serrated margins.
- *Texture.*—Moderate leathery.
- *Aspect.*—Smooth and semi-glossy.
- *Ribs and veins.*—Prominent.
- *Color.*—Upper side — Green, RHS 139A. Under side — Yellow Green, RHS 147B.
- *Petioles.*—About 0.2 cm. long.
- *Stipules.*—Thread-like with glands and about 1.1 cm. long.

Thorns: The plant has thorns of moderate number and slightly curved.
- *Size.*—0.6 cm. long and 0.4 cm. long at base.
- *Color.*—Yellow Green, RHS 146C.

THE BUD

Size: Small.
- *Diameter.*—About 1.5 cm.
- *Length.*—About 2.4 cm.

Shape: Urn-shaped and pointed.
Opening rate: Very slow.
Color:
- *When sepals first divide.*—Red Purple, RHS 67A.
- *When petals begin to unfurl.*—Red Purple, RHS 67B.

Sepals:
- *Number.*—Five.

*Shape.*—Mostly ovate and long acuminate.

*Character.*—The sepals stand up when the bud begins unfurling and about one-fourth open, sepals curl back when bud is about three-fourths open.

*Color.*—Inside — Green, RHS 138C. Outside — Green, RHS 143C.

Calyx:

*Shape.*—Funnel shaped.

*Size.*—Small, about 0.8 cm. wide and about 0.7 cm. long.

*Splitting.*—The calyx does not split.

*Aspect.*—Smooth.

Peduncle of flower stem:

*Length.*—About 7.5 cm. to about 8 cm.

*Character.*—Erect and slender.

*Color.*—Yellow and Green, RHS 144A.

THE FLOWER

Blooming habit: Continuous and profuse year around, blooming freely in fall and also in winter under glass.

Size: Small.

*Diameter.*—About 5.6 to 6.0 cm.

*Depth.*—About 2.5 cm.

Borne: Singly.

Shape: When bloom first opens, cup-shaped. When bloom matures, petals reflex and quill.

Petalage:

*Number.*—About 28 to 30.

*Arrangement.*—Imbricated.

*Form.*—Wide ovate with round apex and reflexed and quilled and with entire margins.

*Texture.*—Leathery.

*Appearance.*—Velvety.

*Color.*—Outer petals: Upper side — Body, Red Purple, RHS 67B. Base, Yellow, RHS 3B. Reverse side — Red Purple, RHS 7C. Inside petals: Upper side — Body, Red Purple, RHS 66A. Base, Yellow, RHS 13C. Reverse side — Body, Red Purple, RHS 67B. Base, Yellow, RHS 3C.

Petaloids:

*Number.*—5 to 9.

*Size.*—Small, about 0.5 cm. long. Large, about 1.4 cm. long.

*Color.*—Red Purple, RHS 66A, with base of Yellow, RHS 13C.

Peduncle:

*Length.*—About 6.5 to 7.8 cm.

*Character.*—Upright and sturdy.

*Color.*—Yellow Green, RHS 144A.

Discoloration after full bloom: The flower holds its color very well.

Persistence: The petals hang on and dry.

Disease resistance: Moderately resistant to mildew, rust and black spot, as observed at both San Leandro and Pleasanton, Calif.

Fragrance: Slight.

Lasting quality: Long, both on the plant and as a cut flower.

REPRODUCTIVE ORGANS

Stamens:

*Number.*—About 60 to 80 in slightly introrse arrangement.

Anthers:

*Size.*—About 0.6 cm.

*Color.*—Yellow Orange, RHS 15B.

Filaments:

*Length.*—About 0.4 cm.

*Color.*—Yellow Orange, RHS 15B.

Pollen:

*Color.*—Yellow Orange, RHS 20A.

Pistils:

*Number.*—About 50 to 70.

Styles:

*Length.*—About 0.3 cm.

*Color.*—Yellow Green, RHS 149B.

Stigmas:

*Color.*—Red, RHS 47B.

Ovaries: Covered with silvery white hair and with individual styles unattached to each other throughout. The calyx tube is ovoid.

I claim:

1. A new and distinct rose plant, substantially as herein shown and described, characterized particularly by its fuchsia purple flowers, its profuse and continuous production of flowers of relatively small size, its rapid growth rate, and its vigorous, upright growth habit.

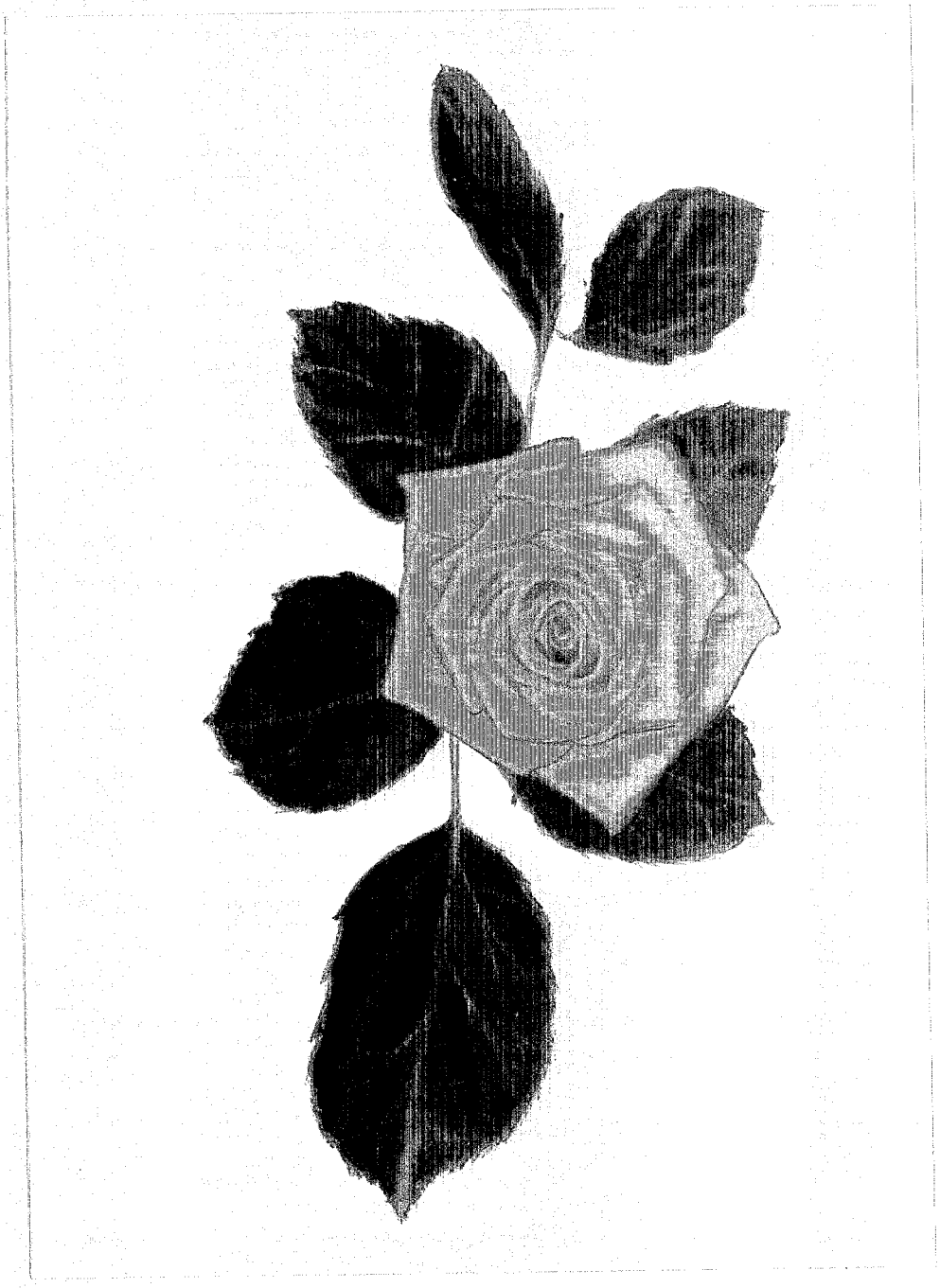

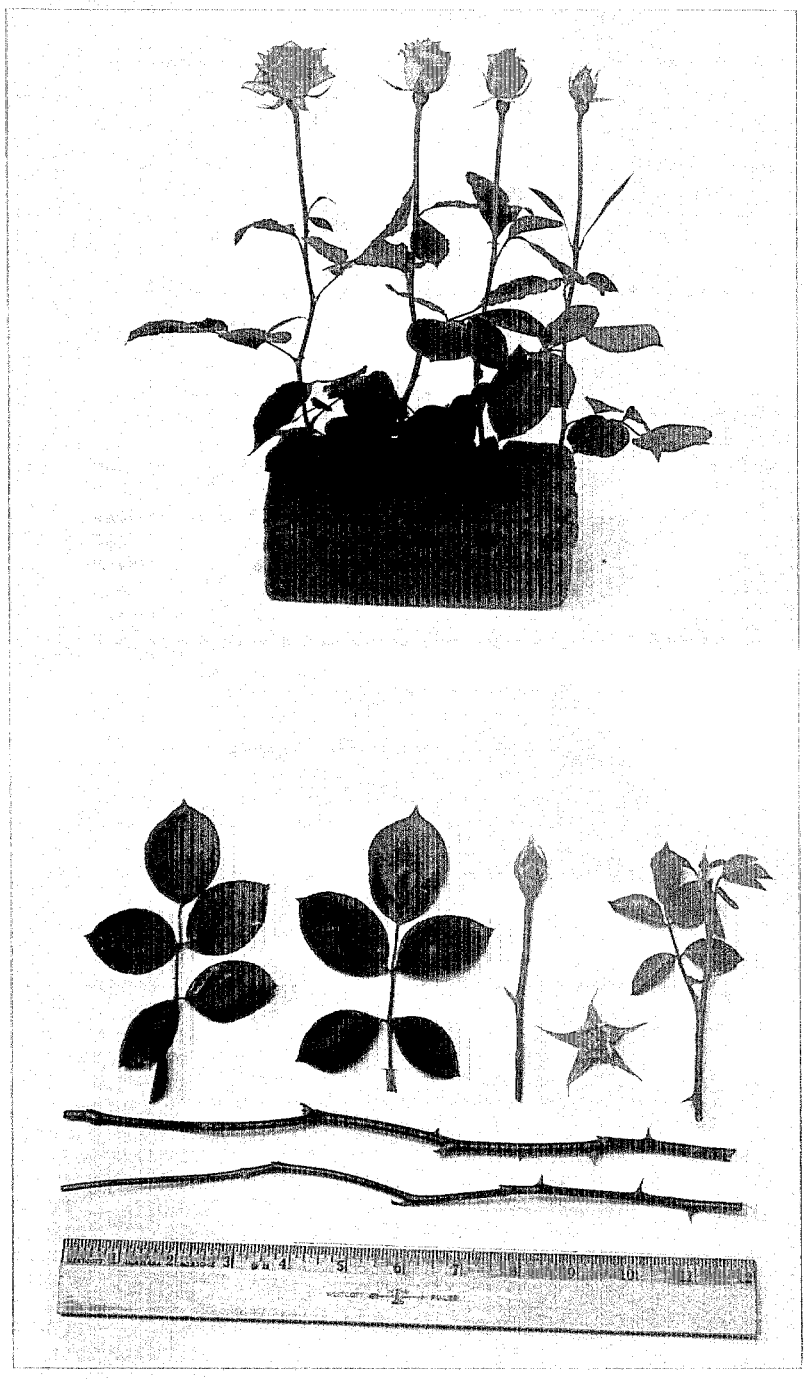

* * * * *